(12) United States Patent
Bui et al.

(10) Patent No.: US 8,609,079 B2
(45) Date of Patent: *Dec. 17, 2013

(54) LONGWEARING, TRANSFER RESISTANT COSMETIC COMPOSITIONS HAVING A UNIQUE CREAMY TEXTURE AND FEEL

(75) Inventors: Hy Si Bui, Piscataway, NJ (US); Susan Halpern, Paramus, NJ (US); Mohamed Kanji, Edison, NJ (US)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/139,547

(22) PCT Filed: Dec. 16, 2009

(86) PCT No.: PCT/US2009/068246
§ 371 (c)(1),
(2), (4) Date: Sep. 7, 2011

(87) PCT Pub. No.: WO2010/077941
PCT Pub. Date: Jul. 8, 2010

(65) Prior Publication Data
US 2011/0311467 A1    Dec. 22, 2011

Related U.S. Application Data

(60) Provisional application No. 61/122,816, filed on Dec. 16, 2008, provisional application No. 61/122,817, filed on Dec. 16, 2008, provisional application No. 61/122,825, filed on Dec. 16, 2008.

(51) Int. Cl.
A61K 31/74 (2006.01)

(52) U.S. Cl.
USPC ........................ 424/78.03; 424/401

(58) Field of Classification Search
USPC ............................... 424/18.03, 401
See application file for complete search history.

(56) References Cited

U.S. PATENT DOCUMENTS

| 4,041,056 | A * | 8/1977 | Heintzelman et al. ........ 554/58 |
| 4,420,588 | A * | 12/1983 | Yoshioka et al. ............ 525/93 |
| 6,482,400 | B1 | 11/2002 | Collin |
| 7,682,621 | B2 | 3/2010 | Lamberty et al. |
| 2006/0159642 | A1 | 7/2006 | Hanna et al. |
| 2007/0259012 | A1 | 11/2007 | Castro et al. |
| 2010/0330012 | A1 | 12/2010 | Bui et al. |
| 2010/0330015 | A1 | 12/2010 | Bui et al. |
| 2010/0330016 | A1 | 12/2010 | Bui et al. |
| 2010/0330017 | A1 | 12/2010 | Bui et al. |
| 2010/0330022 | A1 | 12/2010 | Bui et al. |
| 2010/0330024 | A1 | 12/2010 | Bui et al. |
| 2011/0020254 | A1 | 1/2011 | Bui et al. |
| 2011/0020255 | A1 | 1/2011 | Bui et al. |
| 2011/0020256 | A1 | 1/2011 | Bui et al. |
| 2011/0020257 | A1 | 1/2011 | Bui et al. |
| 2011/0020260 | A1 | 1/2011 | Bui et al. |
| 2011/0020261 | A1 | 1/2011 | Bui et al. |
| 2011/0021681 | A1 | 1/2011 | Bui et al. |
| 2011/0021683 | A1 | 1/2011 | Bui et al. |
| 2011/0038819 | A1 | 2/2011 | Bui et al. |
| 2011/0223122 | A1 | 9/2011 | Bui et al. |
| 2011/0223123 | A1 * | 9/2011 | Bui et al. .............. 424/70.7 |
| 2011/0280817 | A1 | 11/2011 | Ramadan et al. |
| 2011/0280818 | A1 | 11/2011 | Kawaratani et al. |
| 2011/0280820 | A1 | 11/2011 | Bui et al. |
| 2011/0286950 | A1 * | 11/2011 | Bui et al. ............... 424/61 |
| 2011/0286951 | A1 * | 11/2011 | Bui et al. ............... 424/61 |
| 2011/0293550 | A1 * | 12/2011 | Bui et al. .............. 424/70.7 |
| 2012/0107263 | A1 | 5/2012 | Bui et al. |

FOREIGN PATENT DOCUMENTS

JP    07053921 A  *  2/1995

OTHER PUBLICATIONS

U.S. Appl. No. 13/139,846, filed Aug. 10, 2011, Bui, et al.
U.S. Appl. No. 13/140,336, filed Aug. 12, 2011, Bui, et al.
U.S. Appl. No. 13/129,518, filed May 16, 2011, Bui, et al.
U.S. Appl. No. 13/140,306, filed Aug. 10, 2011, Bui, et al.
U.S. Appl. No. 13/139,839, filed Jun. 15, 2011, Bui, et al.
International Search Report issued Aug. 11, 2010 in PCT/US09/68246 filed Dec. 16, 2009.

* cited by examiner

*Primary Examiner* — Ali Soroush
(74) *Attorney, Agent, or Firm* — Oblon, Spivak, McClelland, Maier & Neustadt, L.L.P.

(57) ABSTRACT

The present invention is directed to a long wearing, transfer resistant cosmetic composition which is waterproof, comfortable and has a unique creamy texture and feel containing: (a) a reaction product of (i) at least one polyamine and (ii) at least one oil soluble high carbon polar modified polymer; (b) water; (c) at least one volatile solvent capable of solubilizing the polar modified polymer; (d) optionally at least one non-volatile solvent; and (e) optionally, at least one colorant.

23 Claims, No Drawings

LONGWEARING, TRANSFER RESISTANT COSMETIC COMPOSITIONS HAVING A UNIQUE CREAMY TEXTURE AND FEEL

FIELD OF THE INVENTION

The present invention generally relates to a novel composition which is highly transfer-resistant with excellent long wearing properties which, until now, could only be achieved through the use of silicone resins and traditional film formers. Moreover, the present invention relates to a composition that is easily and uniformly deposited and spread onto a keratinous substrate, having a unique cushiony/bouncy texture and feel.

BACKGROUND OF THE INVENTION

Many compositions, especially cosmetic compositions, have been developed for easy and comfortable application onto a targeted substrate. Unfortunately, many of these compositions are in fact difficult to apply and do not possess a smooth feel upon application. Moreover, compositions often times have a tendency to feel tacky, yielding poor application and spreadability characteristics. Similarly, the use of silicone resins to impart transfer resistance onto a colored cosmetic product suffers from the same disadvantages disclosed above.

In general, a nice texture is typically obtained with the use of expensive silicone elastomers which are swelled in a solvent. The present invention does not require the use of silicone elastomers in order to achieve the desired creamy texture. Moreover, silicone elastomers can also be difficult to formulate with due to their chemical make up, and the gelled compositions they form may be unstable, as is, or sensitive to added ingredients.

Also, in order to obtain a cosmetic composition having good long wear and transfer resistance properties, the use of expensive silicone resins and other conventional film formers, is oftentimes required. The present invention, however, does not require the use of these types of ingredients in order to formulate compositions having good long wear and transfer resistance properties. Significant cost reductions are thus realized due to the relatively inexpensive cost of the ingredients used, as well as the ease in formulating such compositions.

Therefore, it is an object of the present invention to provide a composition capable of possessing a unique creamy texture and feel, having exceptional application properties, even in solid form, while at the same time being long wearing and transfer resistant without having to use silicone resins and other conventional film formers and/or processing techniques, and which can serve as a stable base/matrix for the incorporation of various types of ingredients.

It is also an object of the present invention to provide a composition which is waterproof, highly transfer resistant, easily deposited and spread onto a keratinous substrate while at the same time possessing a unique cushiony/bouncy texture and feel, all without requiring the use of expensive silicone elastomers, silicone resins, gelling agents, or emulsifiers.

BRIEF SUMMARY OF THE INVENTION

The present invention relates to a composition that is capable of possessing a broad range of creamy textures. Furthermore, the present invention relates to a colored cosmetic composition which is highly transfer-resistant with excellent long wearing properties, which until now, could only be achieved through the use of silicone resins and other types of conventional film formers.

The present invention relates to a cosmetic composition comprising: (a) at least one polyamine; (b) at least one oil soluble high carbon polar modified polymer; (c) water; (d) at least one volatile solvent capable of solubilizing the polar modified polymers; (e) optionally at least one non-volatile solvent; and (f) optionally, at least one colorant.

The present invention also relates to a cosmetic composition comprising: (a) a reaction product of (i) at least one polyamine and (ii) at least one oil soluble high carbon polar modified polymer; (b) water; (c) at least one volatile solvent capable of solubilizing the polar modified polymer; (d) optionally at least one non-volatile solvent; and (e) optionally, at least one colorant.

The present invention relates to a cosmetic composition made by combining ingredients comprising: (a) at least one polyamine; (b) at least one oil soluble high carbon polar modified polymer; (c) water; (d) at least one volatile solvent capable of solubilizing the polar modified polymers; (e) optionally at least one non-volatile solvent; and (f) optionally, at least one colorant.

The present invention relates to a cosmetic composition comprising: (a) at least one polyamine; (b) a first oil soluble high carbon polar modified polymer; (c) a second oil soluble high carbon polar modified polymer; (d) water; (e) at least one volatile solvent other than water; (f) optionally at least one non-volatile solvent; and (g) optionally, at least one colorant.

The present invention also relates to a cosmetic composition comprising: (a) a reaction product of (i) at least one polyamine with (ii) a first oil soluble high carbon polar modified polymer; (iii) a second oil soluble high carbon polar modified polymer; (b) water; (c) at least one volatile solvent other than water; (d) optionally at least one non-volatile solvent; and (e) optionally, at least one colorant.

The present invention relates to a cosmetic composition made by combining ingredients comprising: (a) at least one polyamine; (b) a first oil soluble high carbon polar modified polymer; (c) a second oil soluble high carbon polar modified polymer; (d) water; (e) at least one volatile solvent other than water; (f) optionally at least one non-volatile solvent; and (g) optionally, at least one colorant.

A second aspect of the present invention is directed to a method of making up a keratinous substrate involving applying the above-disclosed compositions onto the substrate.

It has been surprisingly discovered that the use of the above-disclosed composition, when applied onto a keratinous substrate, delivers a combination of comfort, stability, and creamy texture and feel, in the absence of expensive silicone elastomers, and in an environmentally-friendly manner, while at the same time being waterproof, long wearing and transfer resistant and not requiring the presence of silicone resins or conventional film formers. It has also been surprisingly discovered that in one embodiment the above-disclosed composition is waterproof, highly transfer resistant, self-emulsifying, easily deposited/spread onto a keratinous substrate, provides excellent coverage thereon, and possesses a unique cushiony/bouncy texture and feel, all without requiring the use of expensive silicone elastomers, silicone resins, other synthetic film formers, gelling agents or emulsifiers. Moreover, the composition serves as an excellent matrix/base for carrying active ingredients.

DETAILED DESCRIPTION OF THE INVENTION

Other than in the operating examples, or where otherwise indicated, all numbers expressing quantities of ingredients and/or reaction conditions are to be understood as being modified in all instances by the term "about".

"Film former" or "film forming agent" or "film forming resin" as used herein means a polymer which, after dissolution in at least one solvent (such as, for example, water and organic solvents), leaves a film on the substrate to which it is applied, for example, once the at least one solvent evaporates, absorbs and/or dissipates on the substrate.

"Tackiness", as used herein, refers to the adhesion between two substances. For example, the more tackiness there is between two substances, the more adhesion there is between the substances.

"Keratinous substrates", as used herein, include but are not limited to, skin, hair and nails.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 37° C., 40° C., 45° C., 50° C., and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Volatile", as used herein, means having a flash point of less than about 100° C.

"Non-volatile", as used herein, means having a flash point of greater than about 100° C.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

Polyamine Compound

According to the present invention, compositions comprising at least one polyamine compound are provided. In accordance with the present invention, the polyamine compound has at least two primary amine groups available to react with hydrophilic groups of the oil-soluble polar modified polymer.

According to particularly preferred embodiments, the polyamine compound is a polyalkyleneimine, preferably a C2-C5 polyalkyleneamine compound, more preferably a polyethyleneimine or polypropyleneimine. Most preferably, the polyalkylenamine is polyethyleneimine ("PEI"). The polyalkyleneamine compound preferably has an average molecular weight range of from 500-200,000, including all ranges and subranges therebetween.

According to preferred embodiments, compositions of the present invention contain polyethyleneimine compounds in the form of branched polymers. Commercially available examples of such polymers are available from BASF under the tradename LUPASOL or POLYIMIN. Non-limiting examples of such polyethyleneimines include Lupasol® PS, Lupasol® PL, Lupasol® PR8515, Lupasol® G20, Lupasol® G35.

According to other embodiments of the present invention, polyamines such as polyethyleneimines and polypropyleneimines can be in the form of dendrimers. Non-limiting examples of such dendrimers are manufactured by the company DSM, and/or are disclosed in U.S. Pat. Nos. 5,530,092 and 5,610,268, the contents of which are hereby incorporated by reference. Commercially available examples of such polymers include polyamidoamine or polypropyleneimine polymers from DENDRITECH sold under the STARBURST® name.

According to other embodiments of the present invention, derivatives of polyalkyleneamines are suitable polyamines. Such derivatives include, but are not limited to, alkylated derivatives, the addition products of alkylcarboxylic acids to polyalkyleneamines, the addition products of ketones and of aldehydes to polyalkyleneamines, the addition products of isocyanates and of isothiocyanates to polyalkyleneamines, the addition products of alkylene oxide or of polyalkylene oxide block polymers to polyalkyleneamines, quaternized derivatives of polyalkyleneamines, the addition products of a silicone to polyalkyleneamines, and copolymers of dicarboxylic acid and polyalkyleneamines. Even further suitable polymamines include, but are not limited to, polyvinylimidazoles (homopolymers or copolymers), polyvinylpyridines (homopolymers or copolymers), compounds comprising vinylimidazole monomers (see, for example, U.S. Pat. No. 5,677,384, hereby incorporated by reference), and polymers based on amino acids containing a basic side chain (preferably selected from proteins and peptides comprising at least 5%, preferably at least 10% of amino acids selected from histidine, lysine and arginine). Such suitable polyamines as described above include those disclosed and described in U.S. Pat. No. 6,162,448, the contents of which are hereby incorporated by reference. Commercially available examples of such polymers include polyvinylamine/formamide such as those sold under the Lupamine® name by BASF, chitosan from vegetable origin such as those sold under the Kiosmetine® or Kitozyme® names, or copolymer 845 sold by ISP.

Preferably, the amount of polyamine compound reacted with the oil-soluble polar modified polymer is such that at least two amine groups on the polyamine compound react with the oil-soluble polar modified polymer to form links or bonds between the amine groups and the hydrophilic groups of the oil-soluble polar modified polymer. The appropriate amount of polyamine compound to react with the oil-soluble polar modified polymer to obtain a reaction product can be easily determined, taking into account the number/amount of reactive amine groups on the polyamine compound and the number/amount of corresponding reactive groups on the oil-soluble polar modified polymer (for example, maleic anhydride groups). According to preferred embodiments, excess oil-soluble polar modified polymer (as determined by the relative number/amount of corresponding reactive groups on the polymer as compared to the reactive amine groups on the polyamine) is reacted with polyamine. Preferably, the polyamine to oil-soluble polar modified polymer ratio is between 0.005 and 1, preferably between 0.006 and 0.5, and preferably between 0.007 and 0.1, including all ranges and subranges therebetween.

The polyamine is typically present in the composition of the invention in an amount ranging from about 0.05 to about 10% by weight, such as from about 1 to about 8% by weight, and from about 2 to about 5% by weight, including all ranges and subranges therebetween, based on the total weight of the composition.

Oil-Soluble High Carbon Polar Modified Polymer

According to the present invention, compositions comprising at least one oil-soluble high carbon polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil. "High carbon" means more than 20 carbon atoms.

Suitable monomers for the hydrophobic homopolymers and/or copolymers include, but are not limited to, cyclic, linear or branched, substituted or unsubstituted, C22-C40 compounds such as, C22-C28 compounds, C24-C26 compounds, C26-C28 compounds, and C30-C38 compounds, including all ranges and subranges therebetween. Preferably, the monomers are C24-26 compounds, C26-C28 compounds or C30-C38 compounds.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to preferred embodiments, the oil-soluble high carbon polar modified polymer is a wax. Also preferably, the oil-soluble high carbon polar modified polymer wax has one or more of the following properties:

a weight-average molecular weight Mw of less than or equal to 30 000 g/mol, preferably of 500 to 10 000 g/mol and particularly preferably of 1000 to 5,000 g/mol, including all ranges and subranges therebetween;

a number-average molecular weight Mn of less than or equal to 15 000 g/mol, preferably of 500 to 12 000 g/mol and particularly preferably of 1000 to 5000 g/mol, including all ranges and subranges therebetween;

a molar mass distribution Mw/Mn in the range from 1.5 to 10, preferably from 1.5 to 5, particularly preferably from 1.5 to 3 and especially preferably from 2 to 2.5, including all ranges and subranges therebetween; and/or a crystallinity of 8% to 60%, preferably 9% to 40%, and more preferably 10% to 30%, including all ranges and subranges therebetween, as determined by differential scanning calorimetry.

According to preferred embodiments relating to a copolymer wax, it is preferable to have, based on the total weight of the copolymer backbone, 0.1 to 30% by weight of structural units originating from the one monomer and 70.0 to 99.9% by weight of structural units originating from the other monomer.

Waxes of the present invention can be based upon homopolymers or copolymers made, for example, by the process described in EP 571 882, the entire contents of which is hereby incorporated by reference. Suitable preparation processes include, for example, suspension polymerization, solution polymerization and gas-phase polymerization of olefins in the presence of catalysts, with polymerization in the monomers also being possible.

Oil-soluble high carbon polar modified polymer wax can be produced in a known manner from the hompopolymers and copolymers described above by oxidation with oxygen-containing gases, for example air, or by graft reaction with polar monomers, for example maleic acid or acrylic acid or derivatives of these acids. The polar modification of polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable oil-soluble high carbon polar modified polymer waxes include, but are not limited to, homopolymers and/or copolymers of C24, C25 and/or C26 groups, copolymers C26, C27 and/or C28 groups, or copolymers of C30-C38 groups, which have been modified with hydrophilic units such as, for example, maleic anhydride, acrylate, methacrylate, polyvinylpyrrolidone (PVP), etc. Preferably, the oil-soluble high carbon polar modified polymer wax has from about 5% to about 30% hydrophilic units, more preferably from about 10% to about 25% hydrophilic units by weight with respect to the weight of the wax, including all ranges and subranges therebetween. Particularly preferred hydrophilically modified waxes are C26, C27 and/or C28 homopolymers and copolymers which have been modified with maleic anhydride units.

Particularly preferred oil-soluble high carbon polar modified polymer waxes for use in the present invention are C26-C28 alpha olefin maleic acid anhydride copolymer waxes commercially available from Clariant under the trade name LICOCARE or LICOCENE. Specific examples of such waxes include products marketed by Clariant under the Lico-Care name having designations such as CM 401, which is a maleic anhydride modified wax having a Mw of 2025 and a crystallinilty of 11%, C30-C38 olefin/isopropylmaleate/maleic anhydride copolymer sold by Baker Hughes under the name Performa® V 1608, and C24-C26 alpha olefin acrylate copolymer wax commercially available from Clariant under the trade name LICOCARE CA301 LP3346 based on a polar backbone with C24-26 side chains with alternating ester and carboxylic acid groups.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orientation (for example, atactic, isotactic or syndiotactic along the backbone).

Preferably, the oil-soluble high carbon polar modified polymer(s) represent from about 1% to about 30% of the total weight of the composition, more preferably from about 3% to about 25% of the total weight of the composition, and most preferably from about 5% to about 20%, including all ranges and subranges therebetween.

Reaction Product

According to preferred embodiments, the oil-soluble polar modified polymer is in an oil carrier, and the polyamine compound is in an aqueous carrier. The reaction occurs by combining the oil carrier and the aqueous carrier. Because the oil-soluble polar modified polymer is typically solid at room temperature, the oil carrier is preferably heated to liquefy the polymer prior to combination with the aqueous carrier. Preferably, the oil carrier is heated beyond the melting point of the oil-soluble polar modified polymer, typically up to about 80° C., 90° C. or 100° C. Although not wanting to be bound by any particular theory, it is believed that at a temperature below 100° C., the reaction of oil-soluble polar modified polymer with the primary amine group of the polyamine opens the anhydride ring to form a half acid and half amide crosslinked product. However, at a temperature above 100° C., the reaction of oil-soluble polar modified polymer with the primary amine group of the polyamine opens the anhydride ring to form an imide crosslinked product. The former product is preferred over the latter product. It is not necessary for all amine groups and all hydrophilic groups to react with each other to form the reaction product. Rather, it is possible that the composition may contain free polyamine and/or free oil-soluble polar modified polymer in addition to the reaction product.

The subsequent reaction product that is formed is surprisingly and unexpectedly capable of forming a film that is long wearing, transfer resistant, self-emulsifying, waterproof, and possessing a unique creamy texture and feel, in the absence of having to use expensive silicone resins, silicone elastomers and other conventional film formers. Moreover, the product is stable, non-sticky/tacky and capable of carrying various types of ingredients.

According to an embodiment of present invention, a first oil soluble high carbon polar modified polymer and a second oil soluble high carbon polar modified polymer are reacted with the polyamine compound, in the presence of water in, at minimum, an amount sufficient to solubilize the polyamine, to form a reaction product. In accordance with the present invention, the reaction product is water-insoluble.

According to preferred embodiments, the first and second oil soluble high carbon polar modified polymer are in an oil carrier, and the polyamine compound is in an aqueous carrier. The reaction occurs by combining the oil carrier and the aqueous carrier. Because the polar modified waxes are typically solid at room temperature, the oil carrier is preferably heated to liquefy the waxes prior to combination with the aqueous carrier. Preferably, the oil carrier is heated beyond the melting point of the oil soluble high carbon polar modified polymers, typically up to about 80° C., 90° C. or 100° C.

Preferably, when the reaction product is exposed to water, water can be incorporated within the reaction product. Thus, rather than forming an aqueous solution when exposed to water, the reaction product preferably maintains its structure. Preferably, the reaction product forms a matrix or carrier containing water. According to preferred embodiments of the present invention, water comprising a desired agent can be incorporated into the reaction product such that the reaction product is a matrix or carrier for the water and/or desired agent.

Although not wanting to be bound by any particular theory, it is also believed that the polyamine(s) can be non-covalently assembled with the polar modified polymer(s) by electrostatic interaction between an amine group of the polyamine and a hydrophilic group (for example, carboxylic acid group associated with maleic anhydride groups) of the polar modified polymer to form a supramolecule. For example, with specific reference to maleic anhydride groups, in the presence of water these groups can open to form dicarboxylic acid groups which can interact with protonated primary amines of the polyamine through ionic interaction to form a polymer-polymer complex with hydrophilic core crosslinkers and a hydrophobic network that act as supramolecular capsule. If a large amount of maleic anhydride groups are present, the secondary amine groups of polyamine are also protonated and interact with alkyl carboxylates.

According to preferred embodiments, the oil-soluble polar modified polymer is in an oil carrier, and the polyamine compound is in an aqueous carrier, and the reaction occurs by combining the oil carrier and the aqueous carrier. Because the oil-soluble polar modified polymer is typically solid at room temperature, the oil carrier is preferably heated to liquefy the polymer prior to combination with the aqueous carrier. Preferably, the oil carrier is heated beyond the melting point of the oil-soluble polar modified polymer, typically up to about 80° C., 90° C. or 100° C.

Without intending to be bound by any particular theory, it is believed that the reason for this is that due to the chemical and physical reactions which take place when the oil-soluble polar modified polymer is combined with the polyamine, the subsequent reaction product that is formed is surprisingly and unexpectedly able to entrap large amounts of water molecules within its hydrophobic matrix. The resultant product is eminently capable of forming a film, is self-emulsifying, waterproof. Moreover, the product is both stable and capable of carrying various types of ingredients.

Volatile Solvents Other than Water

At least one volatile solvent may be chosen from a volatile silicone oil or a volatile non-silicone oil.

Suitable volatile silicone oils include, but are not limited to, linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (3St) from Dow Corning | 102 | 3 |

Suitable volatile non-silicone oils may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

Non-limiting examples of volatile non-silicone oils are listed in Table 2 below.

TABLE 2

| Compound | Flash Point (° C.) |
| --- | --- |
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin C11-C13) | 62 |
| Isopar H (isoparaffin C11-C12) | 56 |

In general, the at least one volatile solvent is preferably present in the composition in an amount of from about 20 to about 90% by weight, such as from about 30 to about 80% by weight, and from about 35 to about 75% by weight, all weights based on the total weight of the composition.

Optional Non-Volatile Solvent

The cosmetic compositions of the present invention comprise optionally at least one non-volatile solvent capable of solubilizing the polar modified polymer. As used herein, the term "non-volatile" means having a flash point of greater than about 100° C. The at least one non-volatile solvent typically comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

Preferably, the non-volatile solvent is present in the cosmetic composition of the invention in an amount of from about 1% to about 95% by weight, such as from about 15% to about 70% by weight, such as from about 25% to about 60% by weight, including all ranges and subranges therebetween, all weights based on the total weight of the composition.

Water

The composition of the present invention also comprises water. The water is preferably employed in an amount of from about 0.5% to about 50% by weight, such as from about 1% to about 8% by weight, such as from about 2% to about 5% by weight, including all ranges and subranges therebetween, all weights based on the total weight of the composition.

Optional Ingredients

The composition of the present invention may also include any one, or more, optional ingredients. Examples thereof include, but are not limited to, colorants such as pigments and dyestuffs, co-solvents, waxes, plasticizers, preservatives, fillers, active ingredients and sunscreens.

The present invention is further described in terms of the following non-limiting examples. Unless otherwise indicated, all parts and percentages are on a weight-by-weight percentage basis.

As can be seen by the following examples, the present invention provides a broad range of creamy textures which are highly transfer-resistant with excellent long wearing properties.

EXAMPLE 1

| INCI Name | EX 1 |
|---|---|
| Isododecane | 69.1 |
| Isohexadecane | 3.9 |
| CA301* | 13 |
| Lupasol G 35 PEI (PolyEthyleneImine) (50% SOLID/50% WATER) | 4 |
| TITANIUM DIOXIDE and DISODIUM | 7.82 |
| IRON OXIDES and DISODIUM | 1.46 |
| IRON OXIDES and DISODIUM | 0.52 |
| IRON OXIDES and DISODIUM | 0.2 |
| Total | 100 |

Example 1 is a creamy gel
*CA301 is a C24-26alpha olefin acrylate copolymer wax commercially available from Clariant under the trade name LICOCARE CA301 LP3346

Procedure:
1. In container A, CA301 was melted in the Isododecane and isohexadecane until fully dissolved. The temperature was brought to 90° C.
2. While maintaining the temperature, the pigment grind were added to container A until fully dissolved.
3. Lupasol G 35 PEI (PolyEthyleneImine) was added at room temperature to container A slowly at high sheer (~700 rpm).
4. Heat was maintained at 70-80° C. for 20 minutes while maintaining high sheer mixing.
5. High sheer mixing was maintained while the batch cooled to room temperature.

EXAMPLES 2-4

| INCI Name | Ex 2 | Ex 3 | Ex 4 |
|---|---|---|---|
| Isododecane | 45.3 | 41.3 | 36.85 |
| Isohexadecane | 3.9 | 3.9 | 5.85 |
| CA301* | 13 | 13 | 19.5 |
| DI Water | 20.5 | 20.5 | 20.5 |
| Lupasol G 35 PEI (PolyEthyleneImine) (50% SOLID/50% WATER) | 4 | 8 | 4 |
| Potassium Cetyl Phosphate | 3 | 3 | 3 |
| Simethicone | 0.3 | 0.3 | 0.3 |
| TITANIUM DIOXIDE and DISODIUM | 7.82 | 7.82 | 7.82 |
| IRON OXIDES and DISODIUM | 1.46 | 1.46 | 1.46 |
| IRON OXIDES and DISODIUM | 0.52 | 0.52 | 0.52 |
| IRON OXIDES and DISODIUM | 0.2 | 0.2 | 0.2 |
| Total | 100 | 100 | 100 |

Example 2 & 3 are creamy gels
Example 4 is a hard gel
*CA301 is a C24-26 alpha olefin acrylate copolymer wax commercially available from Clariant under the trade name LICOCARE CA301 LP3346.

Procedure:
1. In container A, C24-26 Alpha Olefin Acrylate Copolymer was melted in the hydrogenated polydecene and the octyldodecyl neopentanoate until fully dissolved. The temperature was brought to 90° C.
2. While maintaining the temperature, the pigment grind were added to container A until fully dissolved.
3. In a separate container B, Lupasol G 35 PEI (PolyEthyleneImine) and water were mixed at 90° C.
4. Container B was then added to Container A slowly at high sheer (~700 rpm).
5. Heat was maintained at 70-80° C. for 20 minutes while maintaining high sheer mixing.
6. High sheer mixing was maintained while the batch cooled to room temperature.

EXAMPLES 5-9

| INCI Name | Ex 5 | Ex 6 | Ex 7 | Ex 8 | Ex 9 |
|---|---|---|---|---|---|
| Isododecane | 53.75 | 50.7 | 55.7 | 55.7 | 54.725 |
| Isopropyl palmitate | 0 | 5 | 0 | 0 | 0 |
| Isohexadecane | 1.95 | 0 | 0 | 0 | 0.975 |
| CM401* | 0 | 6.5 | 4.35 | 2.15 | 3.25 |
| CA301* | 6.5 | 0 | 2.15 | 4.35 | 3.25 |
| DI Water | 20.5 | 20.5 | 20.5 | 20.5 | 20.5 |
| Lupasol G 35 PEI (PolyEthyleneImine) (50% SOLID/50% WATER) | 4 | 4 | 4 | 4 | 4 |
| Potassium Cetyl Phosphate | 3 | 3 | 3 | 3 | 3 |
| Simethicone | 0.3 | 0.3 | 0.3 | 0.3 | 0.3 |
| TITANIUM DIOXIDE | 7.82 | 7.82 | 7.82 | 7.82 | 7.82 |
| IRON OXIDES | 1.46 | 1.46 | 1.46 | 1.46 | 1.46 |
| IRON OXIDES | 0.52 | 0.52 | 0.52 | 0.52 | 0.52 |
| IRON OXIDES | 0.2 | 0.2 | 0.2 | 0.2 | 0.2 |
| Total | 100 | 100 | 100 | 100 | 100 |

Examples 5-9 are creams
*CM401 is a $C_{26-28}$ α-olefin-maleic acid anhydride copolymer wax commercially available from Clariant under the tradename LICOCARE CM401 LP3345
*CA301 is a $C_{26-28}$ alpha olefin acrylate copolymer wax commercially available from Clariant under the trade name LICOCARE CA301 LP3346

Procedure:
1. In container A, CM401, AND CA301 were melted in the isododecane and isohexadecane until fully dissolved. The temperature was brought to 90° C.
2. While maintaining the temperature, the pigment grind were added to container A until fully dissolved.
3. In a separate container B, Lupasol G 35 PEI (PolyEthyleneImine), optionally the water soluble surfactant, optionally Simethicone, and water were mixed at 90° C.
4. Container B was then added to Container A slowly at high sheer (~700 rpm).
5. Heat was maintained at 70-80° C. for 20 minutes while maintaining high sheer mixing.
6. High sheer mixing was maintained while the batch cooled to room temperature.

What is claimed is:

1. A composition comprising:
   (a) a reaction product of (i) at least one polyamine and (ii) at least one oil soluble high carbon polar modified polymer;
   (b) water;
   (c) at least one volatile solvent capable of solubilizing the polar modified polymer;
   (d) optionally at least one non-volatile solvent; and
   (e) optionally, at least one colorant,
   wherein the polyamine (i) has a molecular weight of from 500-200,000.

2. The composition of claim 1 wherein (i) is a branched polyethyleneimine.

3. The composition of claim 1 wherein (i) is present in an amount of from about 0.05% to about 10% by weight, based on the weight of the composition.

4. The composition of claim 1 wherein (ii) is present in an amount of from about 1% to about 30% by weight, based on the weight of the composition.

5. The composition of claim 1 wherein (b) is present in an amount of from about 0.5% to about 50% by weight, based on the weight of the composition.

6. The composition of claim 1 wherein (c) is a volatile oil.

7. The composition of claim 1 wherein (c) is present in an amount of from about 20 to about 90% by weight, based on the weight of the composition.

8. The composition of claim 1 wherein the composition does not require silicone elastomers, silicone resins or additional film formers.

9. A method of making-up a keratinous substrate comprising applying onto the substrate a composition containing:
   (a) a reaction product of (i) at least one polyamine and (ii) at least one oil soluble high carbon polar modified polymer;
   (b) water;
   (c) at least one volatile solvent capable of solubilizing the polar modified polymers; and
   (d) optionally, at least one non-volatile solvent
   (e) optionally, at least one colorant, wherein the polyamine (i) has a molecular weight of from 500-200,000.

10. A composition, comprising:
    (a) a reaction product of (i) at least one polyamine with (ii) a first oil soluble high carbon polar modified polymer; (iii) a second oil soluble high carbon polar modified polymer;
    (b) water;
    (c) at least one volatile solvent other than water;
    (d) optionally at least one non-volatile solvent; and
    (e) optionally, at least one colorant, wherein the polyamine (i) has a molecular weight of from 500-200,000.

11. The composition of claim 10 wherein (i) is a branched polyethylene imine.

12. The composition of claim 10 wherein (i) is present in an amount of from about 0.05 to about 10% by weight, based on the weight of the composition.

13. The composition of claim 10 wherein (ii) is present in an amount of from about 1 to about 30% by weight, based on the weight of the composition.

14. The composition of claim 10 wherein (iii) is present in an amount of from about 1 to about 30% by weight, based on the weight of the composition.

15. The composition of claim 10 wherein (b) is present in an amount of from about 0.5 to about 50% by weight, based on the weight of the composition.

16. The composition of claim 10 wherein (c) is a volatile oil.

17. The composition of claim 10 wherein (c) is present in an amount of from about 20 to about 90% by weight, based on the weight of the composition.

18. The composition of claim 10 wherein (d) is present in an amount of from about 1 to about 20% by weight, based on the weight of the composition.

19. The composition of claim 10 wherein (e) is present in an amount of from about 3-25% by weight, based on the weight of the composition.

20. The composition of claim 10 wherein the composition does not require silicone elastomers, silicone resins, other synthetic film formers, emulsifiers or gelling agents.

21. A method of making-up a keratinous substrate comprising applying onto the substrate a composition containing:
    (a) a reaction product of (i) at least one polyamine with (ii) a first oil soluble high carbon polar modified polymer; (iii) a second oil soluble high carbon polar modified polymer;
    (b) water;
    (c) at least one volatile solvent other than water;
    (d) optionally, at least one non-volatile solvent; and
    (e) optionally, at least one colorant, wherein the polyamine (i) has a molecular weight of from 500-200,000.

22. The composition of claim 1, wherein the reaction product is a half-acid half-amide reaction product.

23. The composition of claim 10, wherein the reaction product is a half-acid half-amide reaction product.

* * * * *